United States Patent
Fantarella et al.

(10) Patent No.: US 11,318,078 B2
(45) Date of Patent: *May 3, 2022

(54) MOUTHWASH COMPOSITION

(71) Applicant: Fantarella & Harewood, LLC, Hamden, CT (US)

(72) Inventors: Jeralyn R. Fantarella, North Haven, CT (US); Patrick Harewood, West Haven, CT (US)

(73) Assignee: Fantarella & Harewood, LLC, Hamden, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/718,908

(22) Filed: Dec. 18, 2019

(65) Prior Publication Data

US 2020/0121574 A1 Apr. 23, 2020

Related U.S. Application Data

(63) Continuation of application No. 15/530,025, filed on Nov. 21, 2016, now Pat. No. 10,524,993.

(60) Provisional application No. 62/257,356, filed on Nov. 19, 2015.

(51) Int. Cl.
*A61K 8/34* (2006.01)
*A61Q 11/00* (2006.01)
*A61K 8/21* (2006.01)
*A61K 8/24* (2006.01)
*A61K 8/19* (2006.01)
*A61K 8/36* (2006.01)
*A61K 8/90* (2006.01)
*A61K 8/9794* (2017.01)
*A61K 8/365* (2006.01)
*A61K 8/9789* (2017.01)

(52) U.S. Cl.
CPC .............. *A61K 8/345* (2013.01); *A61K 8/19* (2013.01); *A61K 8/21* (2013.01); *A61K 8/24* (2013.01); *A61K 8/36* (2013.01); *A61K 8/365* (2013.01); *A61K 8/90* (2013.01); *A61K 8/9789* (2017.08); *A61K 8/9794* (2017.08); *A61Q 11/00* (2013.01); *A61K 2800/30* (2013.01); *A61K 2800/591* (2013.01)

(58) Field of Classification Search
CPC ...... A61K 8/36; A61K 8/9794; A61K 8/9789; A61K 8/345; A61K 8/365; A61K 8/21; A61K 8/24; A61K 8/90; A61K 8/19; A61K 2800/30; A61K 2800/591; A61Q 11/00
See application file for complete search history.

(56) References Cited

U.S. PATENT DOCUMENTS

| | | |
|---|---|---|
| 3,864,472 A | 2/1975 | Pensak et al. |
| 4,193,988 A | 3/1980 | Forward et al. |
| 4,209,505 A | 6/1980 | Mikhail |
| 4,397,837 A | 8/1983 | Raaf et al. |
| 4,423,030 A | 12/1983 | Hayes et al. |
| 4,612,053 A | 9/1986 | Brown et al. |
| 4,820,506 A | 4/1989 | Kleinberg et al. |
| 4,938,963 A | 7/1990 | Parnell |
| 4,997,654 A | 3/1991 | Corsello et al. |
| 5,009,886 A | 4/1991 | Ahmad et al. |
| 5,039,515 A | 8/1991 | Korf |
| 5,260,282 A | 11/1993 | Attstrom et al. |
| 5,292,527 A | 3/1994 | Konopa |
| 5,378,131 A | 1/1995 | Greenberg |
| 5,560,906 A | 10/1996 | Scodari et al. |
| 5,658,554 A | 8/1997 | Fisher et al. |
| 5,707,610 A | 1/1998 | Ibsen et al. |
| 5,738,113 A | 4/1998 | Connelly |
| 5,817,295 A | 10/1998 | Chaudhari et al. |
| 5,891,448 A | 4/1999 | Chow et al. |
| 5,958,380 A | 9/1999 | Winston et al. |
| 6,022,865 A | 2/2000 | Deutsch |
| 6,174,514 B1 | 1/2001 | Cherukuri et al. |
| 6,200,551 B1 | 3/2001 | Morgan |
| 6,387,352 B1 | 5/2002 | Johansen et al. |
| 6,491,900 B2 * | 12/2002 | Chow .................. A61K 9/0058 424/57 |
| 6,521,264 B1 | 2/2003 | Lacout et al. |
| 7,198,779 B2 | 4/2007 | Rifa Pinol et al. |
| 7,300,645 B2 | 11/2007 | Takatsuka et al. |

(Continued)

FOREIGN PATENT DOCUMENTS

IN 2012DE1376 A 12/2014

*Primary Examiner* — Lezah Roberts
(74) *Attorney, Agent, or Firm* — MKG, LLC

(57) ABSTRACT

A non-alcohol mouthwash composition includes a sweetener, a dispersing agent, a surfactant, an antimicrobial agent, a calcium ion source including calcium lactate, a phosphate ion source including monobasic sodium phosphate, a flavoring agent, a fluoride source, and water. The non-alcohol mouthwash composition includes about 0.001 weight percent of the calcium lactate and about 0.10 weight percent of the monobasic sodium phosphate, based on total weight percent of the non-alcohol mouthwash composition, and the composition has a pH greater than about 5.5. According to embodiments, the non-alcohol mouthwash composition exhibits desirable advantages of being alcohol free, being sodium laural sulfate free, being gluten free, and being substantially 100% natural, as well as alleviating Xerostomia (dry mouth) by stimulating salivary flow, combatting enamel erosion by providing a means of remineralization, providing anticariogenic activity by acting as an antimicrobial agent, and/or providing anti-inflammatory activity, among other benefits.

8 Claims, No Drawings

(56) References Cited

U.S. PATENT DOCUMENTS

| | | |
|---|---|---|
| 7,387,774 B2 | 6/2008 | Faller et al. |
| 8,236,286 B2 | 8/2012 | Yano et al. |
| 8,518,383 B2 | 8/2013 | Haas |
| 8,540,970 B2 | 9/2013 | Rodriguez-Vilaboa |
| 8,580,232 B2 | 11/2013 | Giniger |
| 2005/0287231 A1 | 12/2005 | Nussen |
| 2006/0112584 A1 | 6/2006 | Jones |
| 2006/0263306 A1 | 11/2006 | Pan |
| 2006/0286044 A1 | 12/2006 | Robinson et al. |
| 2009/0252690 A1 | 10/2009 | Behan et al. |
| 2011/0052755 A1 | 3/2011 | Fiorenza et al. |
| 2012/0244086 A1 | 9/2012 | Trivedi et al. |
| 2012/0315226 A1 | 12/2012 | LeGeros et al. |
| 2013/0236400 A1 | 9/2013 | Lewus |
| 2013/0272971 A1 | 10/2013 | Pimenta et al. |
| 2013/0295041 A1 | 11/2013 | Kawa et al. |
| 2013/0344009 A1 | 12/2013 | Nanda |
| 2014/0079750 A1 | 3/2014 | Li et al. |
| 2015/0010481 A1 | 1/2015 | Fujita et al. |

\* cited by examiner

MOUTHWASH COMPOSITION

CROSS REFERENCE TO RELATED APPLICATION

This application is a Continuation application of and claims the benefit under 35 U.S.C. § 120 of U.S. Nonprovisional patent application Ser. No. 15/530,025, filed on Nov. 21, 2016, now U.S. Pat. No. 10524993, issued on Jan. 7, 2020, which claims the benefit under 35 U.S.C. § 119(e) of U.S. Provisional Patent Application Ser. No. 62/257,356, filed on Nov. 19, 2015. The contents of these U.S. patent documents are incorporated herein by reference in their entireties and the benefits of which are fully claimed.

TECHNICAL FIELD

The present disclosure generally relates to mouthwash compositions and, more particularly, to non-alcohol mouthwash compositions.

BACKGROUND

As the mouth cavity is in frequent contact with food, bacteria develops therein which must be addressed with good oral hygiene to reduce the risk of cavities, periodontal disease or other oral diseases. The benefits of brushing and flossing are widely known. However, tooth brushing and flossing may not sufficiently clean all of the teeth surfaces and mouth cavity. Accordingly, mouthwashes are often recommended by professionals, such as dentists and orthodontists, in an effort to combat the adverse effects of bacteria.

Mouthwash, sometimes also referred to as a mouth rinse, is typically a liquid which is not swallowed, but rather swirled within the mouth cavity with use of periodontal muscles or head movement. Commercially available mouthwashes often contain alcohol as an ingredient. However, alcohol can act a drying agent potentially causing dry mouth and increasing halitosis, as well as potentially irritate the mouth cavity. Additionally, mouthwashes containing alcohol may not be suitable for some people such as children.

Accordingly, the inventors under the direction of the present assignee are continually seeking innovations regarding mouthwash compositions in an effort to improve overall oral health and overcome problems associated with some prior mouthwash compositions.

Embodiments of the invention address the foregoing needs and others.

SUMMARY

According to aspects illustrated herein, there is provided a non-alcohol mouthwash composition comprising: a sweetener, a dispersing agent, a surfactant, an antimicrobial agent, a calcium ion source including calcium lactate, a phosphate ion source including monobasic sodium phosphate, a flavoring agent, a fluoride source and water. The non-alcohol mouthwash composition comprises about 0.001 weight percent of the calcium lactate and about 0.10 weight percent of the monobasic sodium phosphate, based on total weight percent of the non-alcohol mouthwash composition, and the non-alcohol mouthwash composition has a pH greater than about 5.5.

According to another aspect illustrated herein, there is provided a non-alcohol mouthwash composition having a pH of greater than about 5.5 and comprising in percent by weight based on total weight percent of the non-alcohol mouthwash composition:

| Ingredient | Percent by Weight (about) |
| --- | --- |
| Water | Balance |
| Glycerin | 36.9 |
| Xylitol | 5.54 |
| Purified Inner Aloe Vera Leaf Powder | 0.04 |
| Potassium sorbate | 0.04 |
| Poloxamer 407 | 0.034 |
| Sodium Fluoride (225 ppm) | 0.046 |
| Calcium lactate | 0.001 |
| Monobasic sodium phosphate | 0.10 |
| Natural ginger flavor extract | 0.0050 to 0.0100 |
| Natural peppermint flavor | 0.050 to 0.100 |
| Natural lime flavor | 0.050 to 0.100 |
| Natural lemon zest flavor | 0.040 to 0.100 | wherein the non-alcohol mouthwash composition has a lemon lime flavor to taste.

According to further aspects illustrated herein, there is provided a non-alcohol mouthwash composition having a pH of greater than about 5.5 and comprising in percent by weight based on total weight percent of the non-alcohol mouthwash composition:

| Ingredient | Percent by Weight (about) |
| --- | --- |
| Water | Balance |
| Glycerin | 25.00 to 30.00 |
| Xylitol | 1.50 to 3.00 |
| Purified Inner Aloe Vera Leaf Powder | 0.02 to 0.06 |
| Potassium sorbate | 0.02 to 0.06 |
| Poloxamer 407 | 0.02 to 0.05 |
| Sodium Fluoride (225 ppm) | 0.010 to 0.030 |
| Calcium lactate | 0.003 to 0.006 |
| Monobasic sodium phosphate | 0.02 to 0.06 |
| Natural ginger flavor extract | 0.0050 to 0.0100 |
| Natural peppermint flavor | 0.050 to 0.100 |
| Natural lime flavor | 0.050 to 0.100 |
| Natural lemon zest flavor | 0.040 to 0.100 | wherein the non-alcohol mouthwash composition has a lemon lime flavor to taste. In some embodiments, the foregoing mouthwash composition is formulated without the afore-recited fluoride and the calcium lactate is between about 0.003 to 0.012 percent by weight.

According to further aspects illustrated herein, there is provided a non-alcohol mouthwash composition having a pH of greater than about 5.5 and comprising in percent by weight based on total weight percent of the non-alcohol mouthwash composition:

| Ingredient | Percent by Weight (about) |
| --- | --- |
| Water | Balance |
| Glycerin | 36.9 |
| Xylitol | 5.54 |
| Purified Inner Aloe Vera Leaf Powder | 0.04 |
| Potassium sorbate | 0.04 |
| Poloxamer 407 | 0.068 |
| Sodium Fluoride (225 ppm) | 0.046 |
| Calcium lactate | 0.001 |
| Monobasic sodium phosphate | 0.10 |
| Natural tamarind flavor | 0.050 to 0.100 |
| Natural lemon zest flavor | 0.040 to 0.100 |
| Natural peppermint flavor | 0.010 to 0.050 | wherein the non-alcohol mouthwash composition has a tamarind flavor to taste.

According to further aspects illustrated herein, there is provided a non-alcohol mouthwash composition having a pH of greater than about 5.5 and comprising in percent by weight based on total weight percent of the non-alcohol mouthwash composition:

| Ingredient | Percent by Weight (about) |
| --- | --- |
| Water | Balance |
| Glycerin | 25.00 to 30.00 |
| Xylitol | 0.50 to 2.00 |
| Purified Inner Aloe Vera Leaf Powder | 0.02 to 0.06 |
| Potassium sorbate | 0.02 to 0.06 |
| Poloxamer 407 | 0.03 to 0.07 |
| Sodium Fluoride (225 ppm) | 0.01 to 0.03 |
| Calcium lactate | 0.003 to 0.006 |
| Monobasic sodium phosphate | 0.02 to 0.06 |
| Natural tamarind flavor | 0.030 to 0.040 |
| Natural lemon zest flavor | 0.040 to 0.100 |
| Natural peppermint flavor | 0.010 to 0.050 | wherein the non-alcohol mouthwash composition has a tamarind flavor to taste. In some embodiments, the foregoing mouthwash composition is formulated without the afore-recited fluoride and the calcium lactate is between about 0.003 to 0.012 percent by weight.

According to further aspects illustrated herein, there is provided a non-alcohol mouthwash composition having a pH of greater than about 5.5 and comprising in percent by weight based on total weight percent of the non-alcohol mouthwash composition:

| Ingredient | Percent by Weight (about) |
| --- | --- |
| Water | Balance |
| Glycerin | 18.5 |
| Xylitol | 5.54 |
| Potassium sorbate | 0.04 |
| Poloxamer 407 | 0.034 |
| Sodium Fluoride (225 ppm) | 0.046 |
| Calcium lactate | 0.001 |
| Monobasic sodium hydrogen phosphate | 0.10 |
| Natural bubble gum flavor | 0.030 to 0.100 |
| Natural peppermint flavor | 0.030 to 0.100 | wherein the non-alcohol mouthwash composition has a bubble gum flavor to taste.

According to further aspects illustrated herein, there is provided a non-alcohol mouthwash composition having a pH of greater than about 5.5 and comprising in percent by weight based on total weight percent of the non-alcohol mouthwash composition:

| Ingredient | Percent by Weight (about) |
| --- | --- |
| Water | Balance |
| Glycerin | 14.0 to 18.0 |
| Xylitol | 1.15 to 3.50 |
| Purified Inner Aloe Vera Leaf Powder | 0.02 to 0.06 |
| Potassium sorbate | 0.02 to 0.06 |
| Poloxamer 407 | 0.02 to 0.05 |
| Sodium Fluoride (225 ppm) | 0.01 to 0.04 |
| Calcium lactate | 0.003 to 0.006 |
| Monobasic sodium hydrogen phosphate | 0.02 to 0.06 |
| Natural bubble gum flavor | 0.030 to 0.100 |
| Natural peppermint flavor | 0.030 to 0.100 | wherein the non-alcohol mouthwash composition has a bubble gum flavor to taste. In some embodiments, the foregoing mouthwash composition is formulated without the afore-recited fluoride and the calcium lactate is between about 0.003 to 0.012 percent by weight.

The above described and other features are exemplified in the detailed description.

DETAILED DESCRIPTION

The inventors have herein developed mouthwash compositions effective in improving overall oral health. Through research and experimentations, the inventors have developed mouthwash compositions which, according to embodiments and as further described below in more detail, exhibit the desirable one or more advantages of, e.g., being alcohol free, being sodium laural sulfate (SLS) free, being gluten free, and being substantially 100% natural, as well as alleviating Xerostomia (dry mouth) by stimulating salivary flow, combatting enamel erosion by providing a means of remineralization, providing anticariogenic activity by acting as an antimicrobial agent, and/or providing anti-inflammatory activity, among other benefits. The mouthwash compositions can also advantageously be tailored to have a variety of tasteful flavors including, but not limited to, lemon lime, tamarind, bubble gum, orange, spearmint, lemon, wild cherry, raspberry, berry mint, ginger, peppermint and/or pineapple.

According to embodiments, a mouthwash composition comprises, e.g., a sweetener, a dispersing agent, a surfactant, an antimicrobial agent, a calcium ion source, a phosphate ion source, a flavoring agent, a fluoride source, balance water. Each of the foregoing ingredients will be described below in more detail.

The sweetener may be any constituent effective in having a destructive effect on Streptococcus mutans and/or other microorganisms associated with tooth decay by inhibiting the ability of the organisms to metabolize carbohydrate. The sweetener also aids in alleviating Xerostomia by increasing salivary flow, and also acts as a remineralization agent. Preferred sweeteners include xylitol.

The dispersing agent may be any constituent effective in promoting a smooth, silky feeling in the mouth. The dispersing agent aids in dispersing, e.g., aloe vera and flavoring agents, as well as aids in providing a flavorful, refreshing and moist feeling to the mouth. Preferred dispersing agents include glycerin.

The surfactant also aids in dispersing, e.g. the flavoring agent(s) throughout the mouthwash in addition to dispersing the mouthwash throughout the oral cavity. Preferred surfactants include Poloxamer 407, which is a hydrophilic non-ionic surfactant of the poloxamer copolymer class. This compound is understood to be a copolymer of a central hydrophobic block of polyethylene glycol (PEG) with two hydrophilic blocks of polyethylene glycol (PEG). Poloxamer 407 is also understood to be sold by BASF under tradename Pluronic® F127.

The antimicrobial agent may be any constituent effective in inhibiting and/or eliminating the growth of microorganism, especially pathogenic microorganisms, in the oral cavity. The antimicrobial agent may also advantageously provide anti-inflammatory effects, e.g. reduction of inflammation from gingivitis. Preferred antimicrobial agents include purified inner aloe vera leaf powder, as well as potassium sorbate.

The calcium ion source advantageously enhances the remineralization capacity of, e.g., Xylitol, in addition to providing calcium ions ($Ca^{2+}$). A preferred calcium ion source is calcium lactate, which promotes remineralization of the tooth enamel.

Similarly, the phosphate ion source also advantageously enhances the remineralization, while also providing phosphate ions. A preferred phosphate ion source is monobasic sodium phosphate. According to the inventors it has surprisingly been determined that including the herein described combination of calcium ion source and phosphate ion source in the mouthwash compositions provides a synergist effect in enhancing the overall effectiveness and pleasantry feel of the mouthwash during use thereby encouraging use and increasing overall oral health of the user. This synergistic effect is especially noticed when about 0.001 weight percent calcium lactate and about 0.10 weight percent weight monobasic sodium phosphate are included in the herein described mouthwash compositions according to the inventors. The inventors have also discovered various phosphate ion sources, for example, monobasic sodium phosphate, contributes and preferably significantly contributes, to raising and maintaining a pH of mouthwash composition of about 5.5, below which demineralization of teeth can occur and thus, contributes to produce a non-alcohol, liquid mouthwash composition having a pH of greater than about 4 and less than about 7, and in embodiments, of about 5.5 and greater.

The flavoring agent included in the mouthwash compositions according to embodiments of the invention may advantageously be any desirable natural flavor/extract imparting the desired flavorful taste to the mouthwash. Flavoring agents include, but are not limited to, the following natural flavor/extracts: lemon lime, tamarind, bubble gum, orange, spearmint, lemon, wild cherry, raspberry, berry mint, peppermint, pineapple, ginger, and any combinations thereof. Advantageously, one or more flavoring agents can be included in the mouthwash compositions according to the invention to provide enhanced customization to suit the user's tastes and preferences, thereby further enhancing overall oral heath as the user will be more inclined to use the mouthwash due to its pleasing taste.

The water constituent acts as a fluid base and flushing mechanism for the herein described mouthwash compositions and is preferably deionized water.

It is further noted that, according to embodiments, a fluoride source such as sodium fluoride is also advantageously included in the mouthwash composition. Fluoride ions from sodium fluoride can also promote remineralization, while also making the tooth more decay resistant and inhibiting bacteria ability to form acids.

Embodiments of the invention will be further understood with reference to the following examples. Accordingly, non-limiting examples of mouthwash compositions according to embodiments of the invention are set forth below in Examples 1-3.

Example 1—Lemon Lime Flavored Mouthwash

The following ingredients are combined and blended uniformly to produce a non-alcohol, liquid mouthwash composition having a pH of greater than about 5.5.

| Ingredient | Percent by Weight (% w/w, about) |
| --- | --- |
| Water | Balance |
| Glycerin | 36.9 |
| Xylitol | 5.54 |
| Purified Inner Aloe Vera Leaf Powder | 0.04 |
| Potassium sorbate | 0.04 |

-continued

| Ingredient | Percent by Weight (% w/w, about) |
| --- | --- |
| Poloxamer 407 | 0.034 |
| Sodium Fluoride (225 ppm) | 0.046 |
| Calcium lactate | 0.001 |
| Monobasic sodium phosphate | 0.10 |
| Natural ginger flavor extract | 0.0067 |
| Natural peppermint flavor | 0.054 |
| Natural lime flavor | 0.054 |
| Natural lemon zest flavor | 0.040 |

The resulting mouthwash advantageously exhibits a flavorful, refreshing lemon lime taste. It is noted that the afore-referenced flavor constituents of the composition of Example 1 could also be varied according to the following ranges (% w/w, about): 0.0050 to 0.0100 Natural ginger flavor extract, 0.050 to 0.100 Natural peppermint flavor, 0.050 to 0.100 Natural lime flavor, and 0.040 to 0.100 Natural lemon zest flavor.

Example 1a—Lemon Lime Flavored Mouthwash

The following ingredients are combined and blended uniformly to produce a non-alcohol, liquid mouthwash composition having a pH of greater than about 5.5.

| Ingredient | Percent by Weight (% w/w, about) |
| --- | --- |
| Water | Balance |
| Glycerin | 28.00 |
| Xylitol | 2.02 |
| Purified Inner Aloe Vera Leaf Powder | 0.04 |
| Potassium sorbate | 0.04 |
| Poloxamer 407 | 0.03 |
| Sodium Fluoride (225 ppm) | 0.0225 |
| Calcium lactate | 0.005 |
| Monobasic sodium phosphate | 0.03 |
| Natural ginger flavor extract | 0.0067 |
| Natural peppermint flavor | 0.054 |
| Natural lime flavor | 0.054 |
| Natural lemon zest flavor | 0.040 |

The resulting mouthwash advantageously exhibits a flavorful, refreshing lemon lime taste. It is noted that the afore-referenced constituents of the composition of Example 1a could also be varied according to the following ranges (% w/w, about): 25.00 to 30.00 Glycerin, 1.50 to 3.00 Xylitol, 0.02 to 0.06 Purified Inner Aloe Vera Leaf Powder, 0.02 to 0.06 Potassium sorbate, 0.02 to 0.05 Poloxamer 407, 0.010 to 0.030 Sodium Fluoride, 0.003 to 0.006 Calcium lactate, 0.02 to 0.06 Monobasic sodium phosphate, 0.0050 to 0.0100 Natural ginger flavor extract, 0.050 to 0.100 Natural peppermint flavor, 0.050 to 0.100 Natural lime flavor, and 0.040 to 0.100 Natural lemon zest flavor.

Example 1b—Lemon Lime Flavored Mouthwash Without Fluoride

The following ingredients are combined and blended uniformly to produce a non-alcohol, liquid mouthwash composition having a pH of greater than about 5.5.

| Ingredient | Percent by Weight (% w/w, about) |
| --- | --- |
| Water | Balance |
| Glycerin | 28.00 |
| Xylitol | 2.02 |
| Purified Inner Aloe Vera Leaf Powder | 0.04 |
| Potassium sorbate | 0.04 |
| Poloxamer 407 | 0.03 |
| Calcium lactate | 0.005 |
| Monobasic sodium phosphate | 0.03 |
| Natural ginger flavor extract | 0.0067 |
| Natural peppermint flavor | 0.054 |
| Natural lime flavor | 0.054 |
| Natural lemon zest flavor | 0.040 |

The resulting mouthwash advantageously exhibits a flavorful, refreshing lemon lime taste without added fluoride. It is noted that the afore-referenced constituents of the composition of Example 1b could also be varied according to the following ranges (% w/w, about): 25.00 to 30.00 Glycerin, 1.50 to 3.00 Xylitol, 0.02 to 0.06 Purified Inner Aloe Vera Leaf Powder, 0.02 to 0.06 Potassium sorbate, 0.02 to 0.05 Poloxamer 407, 0.003 to 0.012 Calcium lactate, 0.02 to 0.06 Monobasic sodium phosphate, 0.0050 to 0.0100 Natural ginger flavor extract, 0.050 to 0.100 Natural peppermint flavor, 0.050 to 0.100 Natural lime flavor, and 0.040 to 0.100 Natural lemon zest flavor.

Example 2—Tamarind Flavored Mouthwash

The following ingredients are combined and blended uniformly to produce a non-alcohol, liquid mouthwash composition having a pH of greater than about 5.5.

| Ingredient | Percent by Weight (% w/w, about) |
| --- | --- |
| Water | Balance |
| Glycerin | 36.9 |
| Xylitol | 5.54 |
| Purified Inner Aloe Vera Leaf Powder | 0.04 |
| Potassium sorbate | 0.04 |
| Poloxamer 407 | 0.068 |
| Sodium Fluoride (225 ppm) | 0.046 |
| Calcium lactate | 0.001 |
| Monobasic sodium phosphate | 0.10 |
| Natural tamarind flavor | 0.054 |
| Natural lemon zest flavor | 0.041 |
| Natural peppermint flavor | 0.014 |

The resulting mouthwash advantageously exhibits a flavorful, refreshing tamarind taste. It is noted that the afore-referenced flavor constituents of the composition of Example 2 could also be varied according to the following ranges (% w/w, about): 0.050 to 0.100 Natural tamarind flavor, 0.040 to 0.100 Natural lemon zest flavor, and 0.010 to 0.050 Natural peppermint flavor.

Example 2a—Tamarind Flavored Mouthwash

The following ingredients are combined and blended uniformly to produce a non-alcohol, liquid mouthwash composition having a pH of greater than about 5.5.

| Ingredient | Percent by Weight (% w/w, about) |
| --- | --- |
| Water | Balance |
| Glycerin | 28.00 |
| Xylitol | 1.12 |
| Purified Inner Aloe Vera Leaf Powder | 0.04 |
| Potassium sorbate | 0.04 |
| Poloxamer 407 | 0.055 |
| Sodium Fluoride (225 ppm) | 0.0225 |
| Calcium lactate | 0.005 |
| Monobasic sodium phosphate | 0.03 |
| Natural tamarind flavor | 0.036 |
| Natural lemon zest flavor | 0.041 |
| Natural peppermint flavor | 0.014 |

The resulting mouthwash advantageously exhibits a flavorful, refreshing tamarind taste. It is noted that the afore-referenced constituents of the composition of Example 2a could also be varied according to the following ranges (% w/w, about): 25.00 to 30.00 Glycerin, 0.50 to 2.00 Xylitol, 0.02 to 0.06 Purified Inner Aloe Vera Leaf Powder, 0.02 to 0.06 Potassium sorbate, 0.03 to 0.07 Poloxamer 407, 0.01 to 0.03 Sodium Fluoride, 0.003 to 0.006 Calcium lactate, 0.02 to 0.06 Monobasic sodium phosphate, 0.030 to 0.040 Natural tamarind flavor, 0.040 to 0.100 Natural lemon zest flavor, and 0.010 to 0.050 Natural peppermint flavor.

Example 2b—Tamarind Flavored Mouthwash without Fluoride

The following ingredients are combined and blended uniformly to produce a non-alcohol, liquid mouthwash composition having a pH of greater than about 5.5.

| Ingredient | Percent by Weight (% w/w, about) |
| --- | --- |
| Water | Balance |
| Glycerin | 28.00 |
| Xylitol | 1.12 |
| Purified Inner Aloe Vera Leaf Powder | 0.04 |
| Potassium sorbate | 0.04 |
| Poloxamer 407 | 0.055 |
| Calcium lactate | 0.005 |
| Monobasic sodium phosphate | 0.03 |
| Natural tamarind flavor | 0.036 |
| Natural lemon zest flavor | 0.041 |
| Natural peppermint flavor | 0.014 |

The resulting mouthwash advantageously exhibits a flavorful, refreshing tamarind taste without added fluoride. It is noted that the afore-referenced constituents of the composition of Example 2b could also be varied according to the following ranges (% w/w, about): 25.00 to 30.00 Glycerin, 0.50 to 2.00 Xylitol, 0.02 to 0.06 Purified Inner Aloe Vera Leaf Powder, 0.02 to 0.06 Potassium sorbate, 0.03 to 0.07 Poloxamer 407, 0.003 to 0.012 Calcium lactate, 0.02 to 0.06 Monobasic sodium phosphate, 0.030 to 0.040 Natural tamarind flavor, 0.040 to 0.100 Natural lemon zest flavor, and 0.010 to 0.050 Natural peppermint flavor.

Example 3—Bubble Gum Flavored Mouthwash

The following ingredients are combined and blended uniformly to produce a non-alcohol, liquid mouthwash composition having a pH of greater than about 5.5.

| Ingredient | Percent by Weight (% w/w, about) |
| --- | --- |
| Water | Balance |
| Glycerin | 18.5 |
| Xylitol | 5.54 |
| Potassium sorbate | 0.04 |
| Poloxamer 407 | 0.034 |
| Sodium Fluoride (225 ppm) | 0.046 |
| Calcium lactate | 0.001 |
| Monobasic sodium hydrogen phosphate | 0.10 |
| Natural bubble gum flavor | 0.032 |
| Natural peppermint flavor | 0.032 |

The resulting mouthwash advantageously exhibits a flavorful, refreshing bubble gum taste. It is noted that the afore-referenced flavor constituents of the composition of Example 3 could also be varied according to the following ranges (% w/w, about): 0.030 to 0.100 Natural bubble gum flavor and 0.030 to 0.100 Natural peppermint flavor.

Example 3a—Bubble Gum Flavored Mouthwash

The following ingredients are combined and blended uniformly to produce a non-alcohol, liquid mouthwash composition having a pH of greater than about 5.5.

| Ingredient | Percent by Weight (% w/w, about) |
| --- | --- |
| Water | Balance |
| Glycerin | 16.00 |
| Xylitol | 2.36 |
| Purified Inner Aloe Vera Leaf Powder | 0.04 |
| Potassium sorbate | 0.04 |
| Poloxamer 407 | 0.02 |
| Sodium Fluoride (225 ppm) | 0.0225 |
| Calcium lactate | 0.005 |
| Monobasic sodium hydrogen phosphate | 0.03 |
| Natural bubble gum flavor | 0.064 |
| Natural peppermint flavor | 0.032 |

The resulting mouthwash advantageously exhibits a flavorful, refreshing bubble gum taste. It is noted that the afore-referenced constituents of the composition of Example 3a could also be varied according to the following ranges (% w/w, about): 14.0 to 18.0 Glycerin, 1.15 to 3.50 Xylitol, 0.02 to 0.06 Purified Inner Aloe Vera Leaf Powder, 0.02 to 0.06 Potassium sorbate, 0.02 to 0.05 Poloxamer 407, 0.01 to 0.04 Sodium Fluoride, 0.003 to 0.006 Calcium lactate, 0.02 to 0.06 Monobasic sodium hydrogen phosphate, 0.030 to 0.100 Natural bubble gum flavor and 0.030 to 0.100 Natural peppermint flavor.

Example 3b—Bubble Gum Flavored Mouthwash without Fluoride

The following ingredients are combined and blended uniformly to produce a non-alcohol, liquid mouthwash composition having a pH of greater than about 5.5.

| Ingredient | Percent by Weight (% w/w, about) |
| --- | --- |
| Water | Balance |
| Glycerin | 16.00 |
| Xylitol | 2.36 |
| Purified Inner Aloe Vera Leaf Powder | 0.04 |
| Potassium sorbate | 0.04 |
| Poloxamer 407 | 0.02 |
| Calcium lactate | 0.005 |
| Monobasic sodium hydrogen phosphate | 0.03 |
| Natural bubble gum flavor | 0.064 |
| Natural peppermint flavor | 0.032 |

The resulting mouthwash advantageously exhibits a flavorful, refreshing bubble gum taste without added fluoride. It is noted that the afore-referenced constituents of the composition of Example 3b could also be varied according to the following ranges (% w/w, about): 14.0 to 18.0 Glycerin, 1.15 to 3.50 Xylitol, 0.02 to 0.06 Purified Inner Aloe Vera Leaf Powder, 0.02 to 0.06 Potassium sorbate, 0.02 to 0.05 Poloxamer 407, 0.003 to 0.012 Calcium lactate, 0.02 to 0.06 Monobasic sodium hydrogen phosphate, 0.030 to 0.100 Natural bubble gum flavor and 0.030 to 0.100 Natural peppermint flavor.

It is noted that the pH of the mouthwash compositions according to embodiments of the invention may vary and is typically greater than about 4 and less than about 7. For example, the pH of lemon lime flavored mouthwash and tamarind flavored mouthwash according to some embodiments is about 5.8. The pH of bubble gum flavored mouthwash according to some embodiments is about 6.2. According to the inventors, if the pH falls below about 5.5 demineralization of the teeth may occur. Moreover, sorbates are relatively ineffective at a pH of greater than or equal to about 7.0 and sorbates are also more effective than sodium benzoate at a pH greater than about 4.0 according to the inventors.

According to embodiments, the mouthwash compositions are prepared by, e.g., adding the Xylitol, aloe vera, potassium sorbate, sodium fluoride, calcium lactate, sodium phosphate and glycerin to the water, and mixing for about two minutes. The Polyoxamer 407 is then added and mixed until totally dispersed, followed by addition of the flavoring agents and mixing thoroughly, according to embodiments.

Advantageously, embodiments according to the invention can improve overall oral health of the user.

Another advantage of embodiments of the invention includes a synergistic effect of the constituents. For example, xylitol and potassium sorbate when combined can work together to effect and/or to enhance antimicrobial properties. Similarly, the xylitol and sodium fluoride when combined can also work together to further effect and/or enhance the antimicrobial properties. The synergistic effect of the constituents can be further seen by the combination of xylitol and sodium fluoride to advantageously provide remineralization effects. The inventors have also discovered that various phosphate ion sources, for example, monobasic sodium phosphate, contributes and preferably significantly contributes, to raising and maintaining a pH of mouthwash composition of about 5.5, below which demineralization of teeth can occur and thus, contributes to produce a non-alcohol, liquid mouthwash composition having a pH of greater than about 4 and less than about 7, and in embodiments, of about 5.5 and greater.

A further advantage is that the mouthwash compositions according to embodiments of the invention are alcohol free, as well as gluten free. A still further advantage is that the mouthwash compositions according to embodiments of the invention inhibited the growth of bacteria cells in the mouth. Thus, according to embodiments, also disclosed is a method of inhibiting growth of bacteria cells in the mouth utilizing any of the herein described mouthwash compositions. For example, according to embodiments, any mouthwash composition as described herein may be swirled in the mouth cavity to advantageously disperse the constituents throughout the mouth cavity and over the teeth and gums. Then, the mouthwash composition may be discarded from the mouth, typically without swallowing any significant amount of the composition.

While the invention has been described with reference to various exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims.

Moreover, it is noted that the features and elements described herein can be employed in any combination with other features and/or elements, embodiments and so forth described herein.

Additionally, according to embodiments, the herein recited mouthwash compositions can "comprise," "consist of" or "consist essentially of" the constituents recited therein.

Also, the terms "non-alcohol" and "alcohol free" are herein intended to mean that alcohol is not intentionally added to the herein described mouthwash compositions as an ingredient, and "non-alcohol" and "alcohol free" could include mere traces of alcohol.

What is claimed is:

1. A non-alcohol mouthwash composition having a pH of greater than about 5.5 and comprising in percent by weight based on total weight percent of the non-alcohol mouthwash composition:

| Ingredient | Percent by Weight (about) |
|---|---|
| Water | Balance |
| Glycerin | 25.00 to 30.00 |
| Xylitol | 1.50 to 3.00 |
| Purified Inner Aloe Vera Leaf Powder | 0.02 to 0.06 |
| Potassium sorbate | 0.02 to 0.06 |
| Poloxamer 407 | 0.02 to 0.05 |
| Sodium Fluoride (225 ppm) | 0.010 to 0.030 |
| Calcium lactate | 0.003 to 0.006 |
| Monobasic sodium phosphate | 0.02 to 0.06 |
| Natural ginger flavor extract | 0.0050 to 0.0100 |
| Natural peppermint flavor | 0.050 to 0.100 |
| Natural lime flavor | 0.050 to 0.100 |
| Natural lemon zest flavor | 0.040 to 0.100 | wherein the non-alcohol mouthwash composition has a lemon lime flavor to taste.

2. The non-alcohol mouthwash composition of claim 1 comprising, in weight percent, about 28.00 Glycerin, about 2.02 of the Xylitol, about 0.04 of the Purified inner aloe vera leaf powder, about 0.04 of the Potassium sorbate, about 0.03 of the Poloxamer 407, about 0.0225 of the Sodium fluoride, about 0.005 of the Calcium lactate, about 0.03 of the Monobasic sodium phosphate, about 0.0067 of the Natural ginger flavor extract, about 0.054 of the Natural peppermint flavor, about 0.054 of the Natural lime flavor, and about 0.040 of the Natural lemon zest flavor.

3. The non-alcohol mouthwash composition of claim 1, wherein the non-alcohol mouthwash composition stimulates salivary flow and alleviates dry mouth.

4. The non-alcohol mouthwash composition of claim 1, wherein the non-alcohol mouthwash composition combats enamel erosion.

5. The non-alcohol mouthwash composition of claim 1, wherein the non-alcohol mouthwash composition acts as an antimicrobial agent.

6. The non-alcohol mouthwash composition of claim 1, wherein the non-alcohol mouthwash composition provides anti-inflammatory activity.

7. The non-alcohol mouthwash composition of claim 1, wherein the non-alcohol mouthwash composition inhibits growth of bacteria cells.

8. A non-alcohol mouthwash composition having a pH of greater than about 5.5 and comprising in percent by weight based on total weight percent of the non-alcohol mouthwash composition:

| Ingredient | Percent by Weight (about) |
|---|---|
| Water | Balance |
| Glycerin | 25.00 to 30.00 |
| Xylitol | 1.50 to 3.00 |
| Purified Inner Aloe Vera Leaf Powder | 0.02 to 0.06 |
| Potassium sorbate | 0.02 to 0.06 |
| Poloxamer 407 | 0.02 to 0.05 |
| Calcium lactate | 0.003 to 0.012 |
| Monobasic sodium phosphate | 0.02 to 0.06 |
| Natural ginger flavor extract | 0.0050 to 0.0100 |
| Natural peppermint flavor | 0.050 to 0.100 |
| Natural lime flavor | 0.050 to 0.100 |
| Natural lemon zest flavor | 0.040 to 0.100 | wherein the non-alcohol mouthwash composition has a lemon lime flavor to taste.

* * * * *